(12) United States Patent
Lococo

(10) Patent No.: US 7,776,099 B2
(45) Date of Patent: Aug. 17, 2010

(54) BONE IMPLANT AND DEVICE FOR FORMING A SOCKET FOR SAME

(76) Inventor: Michael Lococo, 4674 St. Claire, Niagara Falls, Ontario (CA) L2E 3S8

( * ) Notice: Subject to any disclaimer, the term of this patent is extended or adjusted under 35 U.S.C. 154(b) by 1293 days.

(21) Appl. No.: 10/542,413

(22) PCT Filed: Jan. 6, 2004

(86) PCT No.: PCT/CA2004/000016

§ 371 (c)(1),
(2), (4) Date: Dec. 1, 2005

(87) PCT Pub. No.: WO2004/062535

PCT Pub. Date: Jul. 29, 2004

(65) Prior Publication Data

US 2006/0106388 A1    May 18, 2006

(30) Foreign Application Priority Data

Jan. 14, 2003    (CA) .................................. 2416348

(51) Int. Cl.
*A61F 2/28* (2006.01)
(52) U.S. Cl. ................................................. 623/23.48
(58) Field of Classification Search .... 623/17.11–17.16
See application file for complete search history.

(56) References Cited

U.S. PATENT DOCUMENTS

| | | | | |
|---|---|---|---|---|
| 5,013,242 A | | 5/1991 | Prezmecky | .................. 433/174 |
| 5,580,353 A | * | 12/1996 | Mendes et al. | ........... 623/20.18 |
| 5,766,009 A | | 6/1998 | Jeffcoat | ...................... 433/173 |

FOREIGN PATENT DOCUMENTS

| | | |
|---|---|---|
| DE | 3533432 | 3/1987 |
| DE | 19816832 | 1/2000 |
| WO | WO 00/74607 A1 | 12/2000 |

* cited by examiner

*Primary Examiner*—David Isabella
*Assistant Examiner*—Ann Schillinger
(74) *Attorney, Agent, or Firm*—Winston & Strawn LLP

(57) ABSTRACT

A bone implant having a core section to which a prosthesis is eventually secured, and rib-like projections or anchoring prongs enhancing the hold of the implant in the bone. The invention is particularly, but not exclusively, intended as a dental implant. The socket for the implant is drilled in a bone using a suitable template which is subsequently inserted in an original pre-drilled bore and which serves as a guide for subsequent drilling of bores for the anchoring prongs or rib-like projections. Several different types of the templates are disclosed together with a number of compatible implants. A specific tool is also disclosed which reduces the damage to the bone by reducing the volume of the initial portion of the socket adapted to receive the associated template.

18 Claims, 14 Drawing Sheets

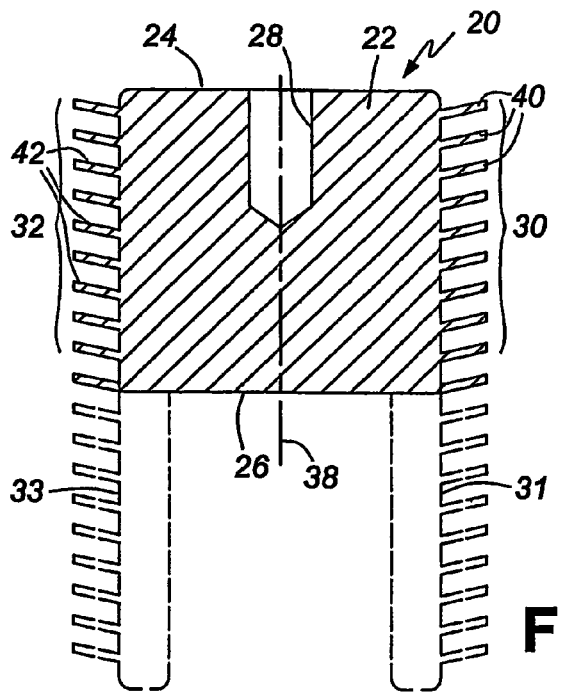
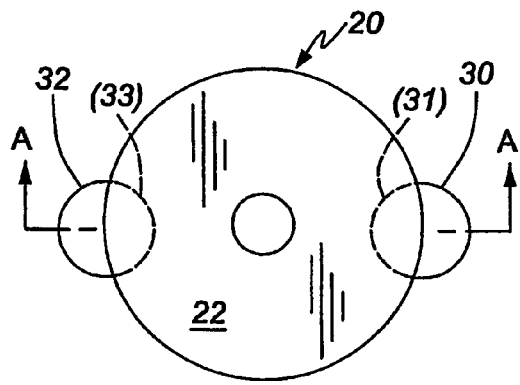
FIG. 1
FIG. 2
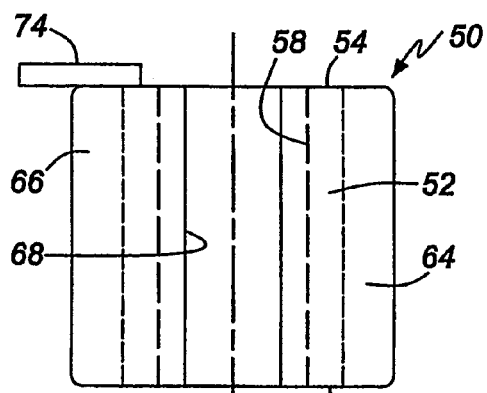
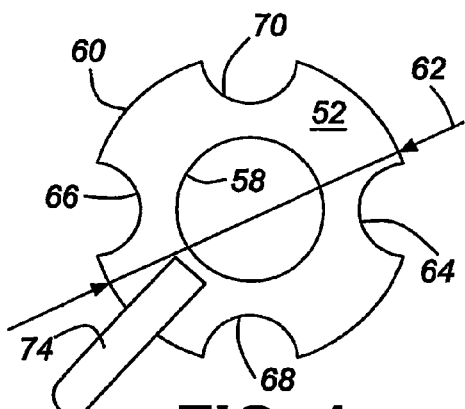
FIG. 3
FIG. 4
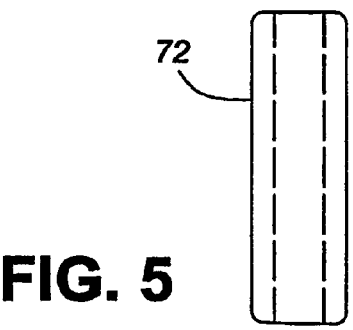
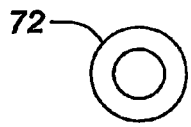
FIG. 5
FIG. 6

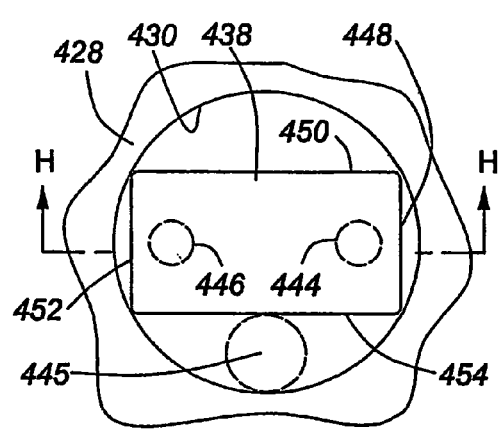
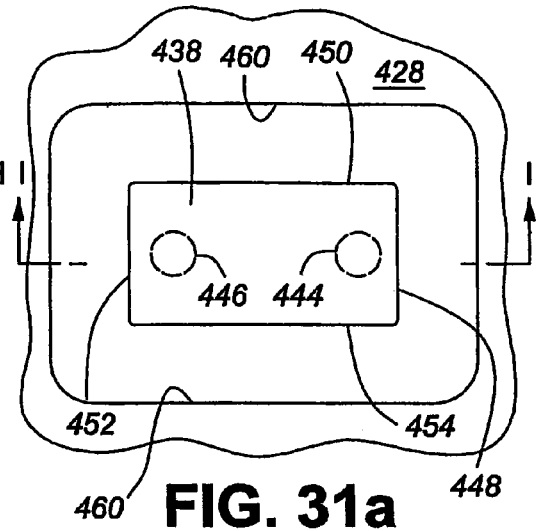
FIG. 30a  FIG. 31a
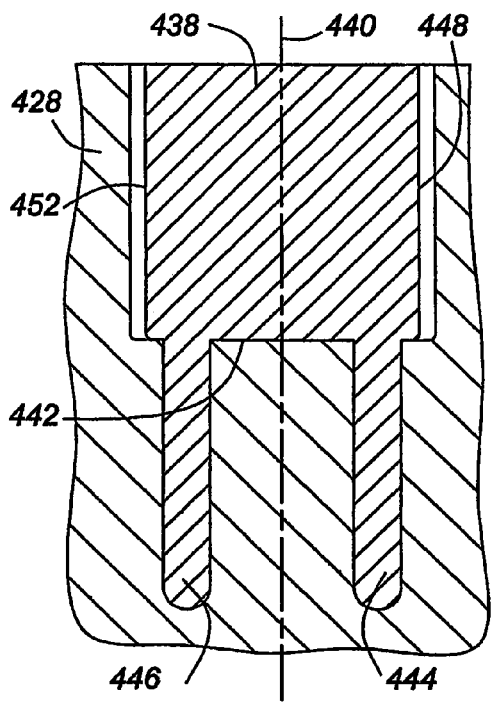
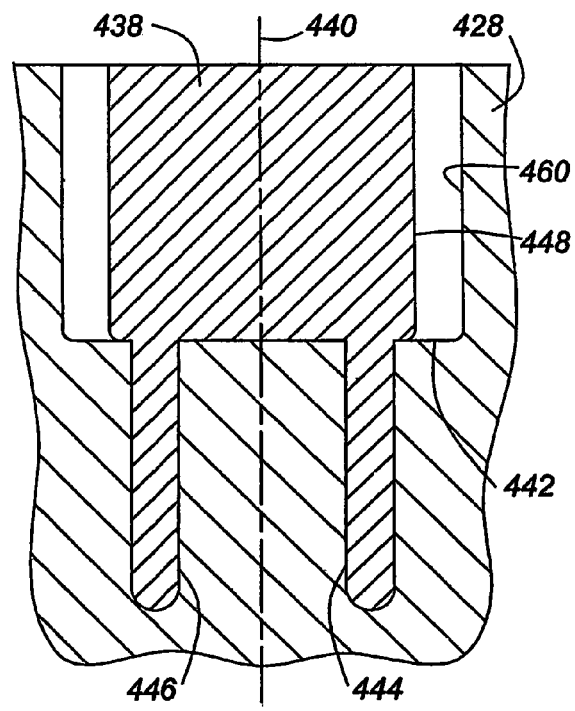
FIG. 30b  FIG. 31b

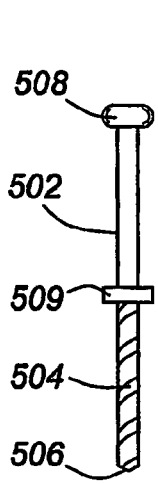
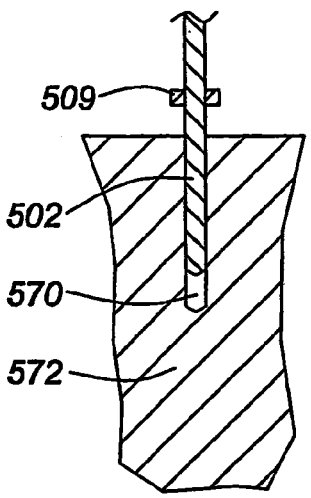
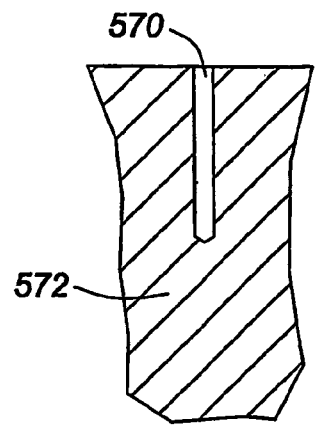
FIG. 33  FIG. 34  FIG. 35
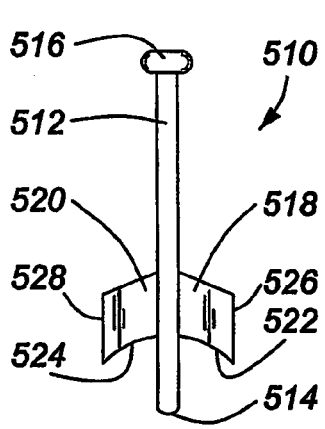
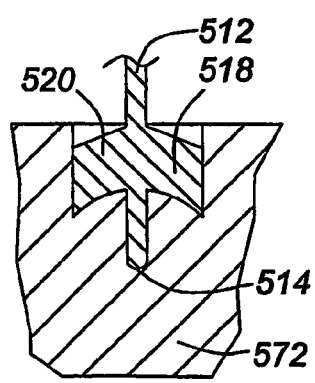
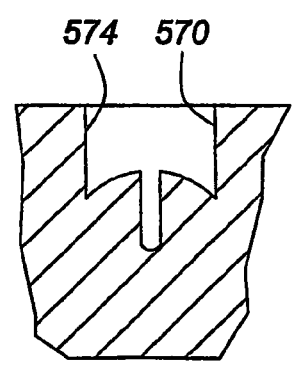
FIG. 36  FIG. 38  FIG. 39
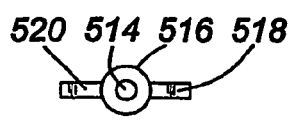
FIG. 37

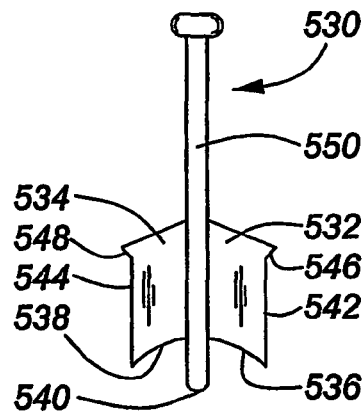
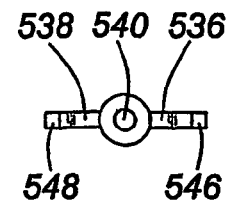
FIG. 40  FIG. 41
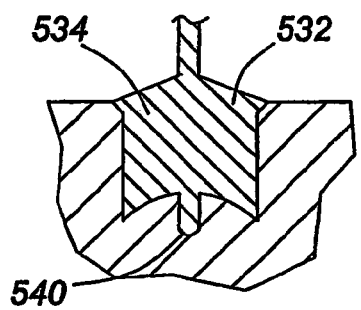
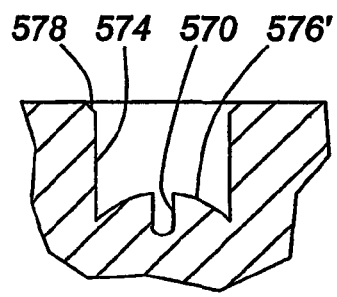
FIG. 42  FIG. 43

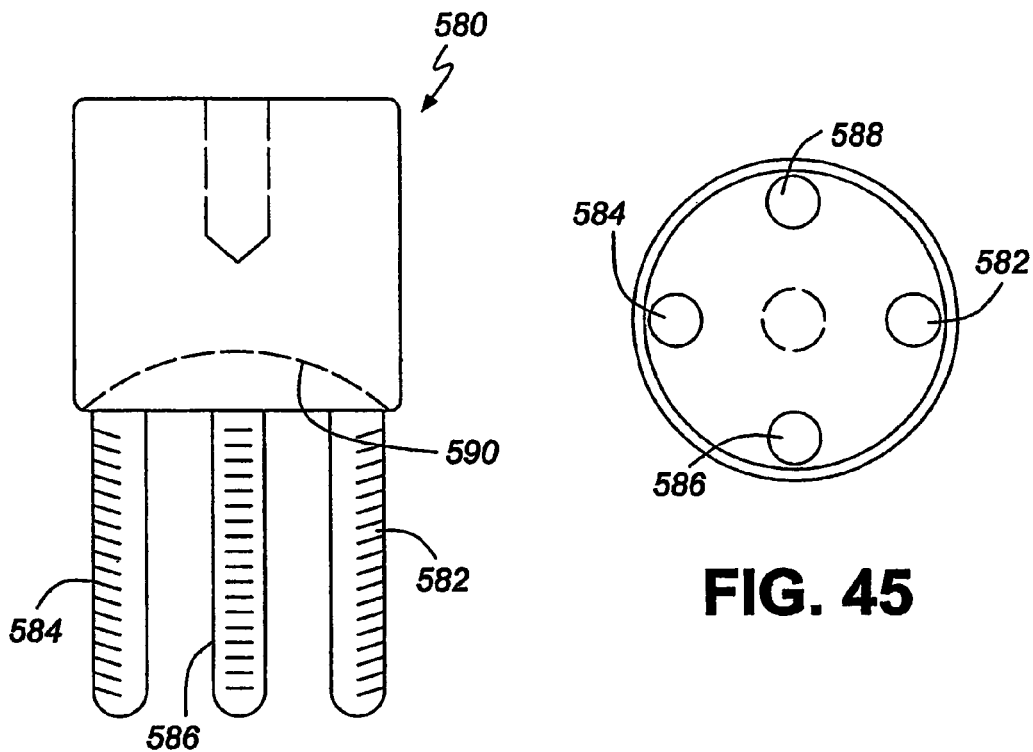
FIG. 44
FIG. 45
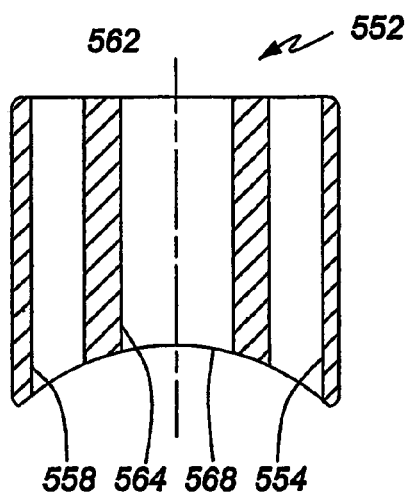
FIG. 46
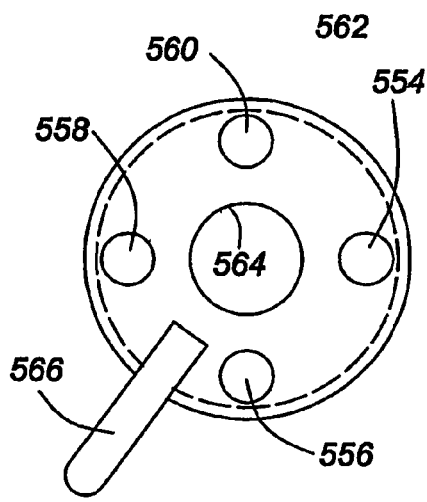
FIG. 47

BONE IMPLANT AND DEVICE FOR FORMING A SOCKET FOR SAME

BACKGROUND

The present invention relates to the art of bone implants and devices and methods for forming, in a bone, a socket for receiving same.

It is known to provide various types of bone implants used in dentistry, joint prostheses installation or other branches of medicine. In most cases, the bone implant is used as an anchor in the bone for an extension secured to the top surface of the implant. A typical example of such implant is presented by implants used in dentistry but the present invention is not limited to that particular field of medicine.

The known bone implants are of two basic types. First, an implant is simply screwed into a pre-drilled bore by self-tapping action during which the thread of the implant taps into the surrounding bone often causing substantial damage to the bone tissue surrounding the implant and thus retarding the healing process. Another implant, used often in installation of the artificial joint head to a femur, is simply an elongated, slightly tapered stem driven by impact force into the marrow of the femur destroying a considerable part of the marrow. It is also known to provide what basically amounts to a bolt-and-nut securement of the implant used in supporting the head of an artificial hip joint. Such arrangement again uses a considerable space and its installation often results in substantial destruction of the bone and marrow tissue in the vicinity of the implant.

It is an object of the present invention to provide a bone implant which would provide a firm securement to the bone tissue without subjecting the bone or the marrow to undue damage caused by the installation process.

SUMMARY OF THE INVENTION

In general terms, the invention provides, in one aspect thereof, a bone implant which comprises (1) a core having a first end, a second end and defining a centerline extending centrally of and between said ends, and a circumferential side wall portion extending between said ends and being parallel with the centerline; (2) at least two elongated projections extending from said core and having a rounded contour when viewed in axial direction of said centerline.

The rib-like projections may take the shape of ribs extending from the circumferential side wall. If desired, the ribs may extend beyond the second end of the core by way of anchoring stems. Another modification is devoid of the ribs. The rib-like projections are stems projecting from the second end of the core at locations slightly spaced radially inwardly from the circumference of the second end. The projections may be formed by a plurality of fins disposed in a row parallel with the axis of the core or with elongation of the respective stem. The stems projecting from the core can either be parallel with the axis of the core or at least one of the stems may extend obliquely away from the core. The core may have a circular cross-section perpendicular to its axis, or it may be of a radially elongated shape, for instance, oval, or even multilateral, particularly rectangular with rounded corners.

In another aspect, the invention provides template means for use in forming a socket in a bone into which the respective implant may be tapped. The template means may comprise a template formed by a sleeve having an axis, a first end, a second end, an inner wall and an outer wall. The outer wall corresponds in shape and size to the circumferential side wall of the respective implant. At least two axially elongated channels or grooves of a semi-circular cross-section are formed in the outer wall to serve as drill guides. They extend parallel with the axis of the template. The template means further includes a generally cylindric locking pin discrete from the sleeve and compatible in radius with one or all of said grooves.

In another embodiment of the template means, the axially elongated channels are bores extending from the first end to the second end and disposed inwards of the circumferential wall, to guide drill bits forming bores in the bone for receiving the stems.

Yet another embodiment of the template means comprises, in addition to the previously mentioned template, a template having an oblique guide channel extending through a core between the first and second ends thereof. At the same time, this template has a locking stem projecting from the second end to prevent inadvertent turning of the template about its axis.

In a particularly preferred embodiment, it is proposed that the core of the implant and of the template be concavely curved at the second end and that the corresponding bore in the bone be formed with a convex bottom using new tools which are also subject to the present invention.

In particular, the tools for drilling the last mentioned bore for the core of the implant are shaped drill bits having each a centrally disposed cylindric stem at a free end and a pair of radially projecting, opposed cutting plates which are provided with a concavely curved cutting plate turned towards the free end of the tool. The plates of the formed tool thus resemble the cutting wings of what is known as a spade bit. The cylindric stem has a small diameter corresponding to that of a drill for making a pilot bore for guiding the shaped drill bit or bits.

BRIEF DESCRIPTION OF THE DRAWINGS

Further features and advantages of the different embodiments of the invention will become apparent from the following description, referring to the accompanying diagrammatic, simplified and not-to-scale drawings. The drawings depict:

FIG. 1 a cross-sectional view, taken along the section line A-A of FIG. 2, depicting a first and second embodiment of the implant of the present invention, the features of the second embodiment additional to those of the first embodiment being diagrammatically shown in broken lines;

FIG. 2 a top plan view of FIG. 1;

FIG. 3 a side view of a template of template means used in forming a socket for receiving the implant shown in FIGS. 1 and 2;

FIG. 4 a top plan view thereof;

FIG. 5 a side view of a locking pin of the template means;

FIG. 6 a top plan view of FIG. 5;

FIG. 28b a diagrammatic cross-section F-F of FIG. 28a;

FIG. 29a top plan view of a first template of template means for forming a socket for the implant of FIG. 27;

FIG. 30a a top plan view of a second template of template means for forming a socket for the implant of FIG. 27, the second template being shown inserted in the pilot bore of FIG. 29;

FIG. 30b a cross-section H-H of FIG. 30a;

FIG. 31a is a view similar to that of FIG. 30a but showing the pilot bore enlarged to correspond in shape and size to the circumference of the core of the implant of FIG. 27;

FIG. 31b a section I-I of FIG. 31a;

FIG. 32b section J-J of FIG. 32a;

FIG. 33 a side view of a drill bit for preparing a pilot bore for the implant of FIG. 44;

FIG. 34 a section view showing the drill of FIG. 33 at the time of a partial withdrawal from a finished pilot bore;

FIG. 35 a section view similar to FIG. 34 but showing only the pilot bore;

FIG. 36 a side view of a first shaped bit for forming a socket for the core of the implant FIG. 44;

FIG. 37 a bottom plan view of FIG. 36;

FIG. 38 a section view similar to FIG. 34 showing the first shaped bit in a terminal inward position;

FIG. 39 a view similar to FIG. 35 but showing the stage where the implant socket has been partly formed by the first shaped bit;

FIG. 40 a view similar to FIG. 36 but showing a second shaped bit for forming the implant socket;

FIG. 41 a bottom plan view of FIG. 40;

FIG. 42 a section view similar to that of FIG. 38 showing the second shaped bit in a terminal inward position;

FIG. 43 a view similar to FIG. 39 but showing a portion of the socket for receiving a core of the implant of FIG. 44;

FIG. 44 a side view, not to scale, of an implant for eventual placement in the socket of FIG. 43;

FIG. 45 a bottom plan view of FIG. 44;

FIG. 46 a section view showing a template for forming bores for anchoring stems of the implant of FIG. 44; and FIG. 47 a top plan view of the template of FIG. 46.

DETAILED DESCRIPTION OF THE PREFERRED EMBODIMENTS

Figure 7:
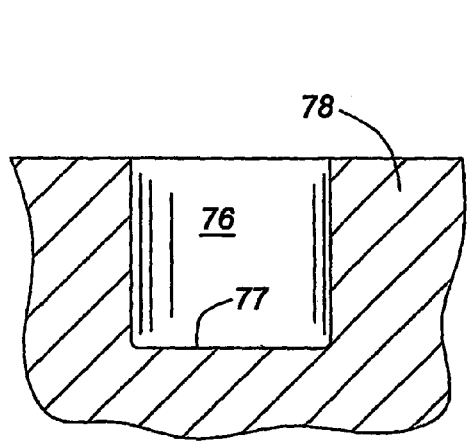
FIG. 7 a diagrammatic section of a bone with a pre-drilled bore for the core of an associated implant.

Turning now to FIG. 1, reference number 20 designates the first and second embodiment of the inventive implant, with additional structural features of second embodiment shown in broken lines. The implant is made of titanium or any other material suitable for the purpose. The description of the first embodiment relates to a dental implant but it will be appreciated that other than dental applications of the implant may exist.

The implant 20 includes a core 22. The core 22 is solid and defines a first end 24, a second end 26 and a centerline 38 extending centrally of and between the ends 24, 26. In the embodiment shown, two rib-like projections 30-32 having an axial elongation, parallel with the axis 38, project radially outwards from the circumferential wall 34 of the core 22, and, longitudinally from the first end 24 to the second end 26. In a modified embodiment, the projections extend beyond the second end, defining two anchoring extensions or stems 31, 33. The circumferential wall 35 is parallel with the axis 38. In the embodiment shown, the wall 35 is cylindric, having a circular cross-section but other shapes, e.g. an oval or multilateral, cross-sectional configurations of the wall 35 are possible.

The first end 24 of the core 22 is provided with a securement means, for instance a threaded bore 28 for fixing a respective prosthesis or healing cap to the core 22. For clarity, the projections 30-32 may also be designated as a first and second, projection, respectively.

The projections 30-32 may be solid ribs of rounded contour as shown in FIG. 2, integrally formed with the core 22. It is preferred, however, that the ribs be each formed, at least over a part of their overall length, by a straight row of fins 40, 42 having an inclination shown in FIG. 1. In other words, the fins 40, 42 slope at a slight angle of inclination in a direction radially inwards and axially away from the first end 24. This provides the fins with a back biting feature which impedes the withdrawal of the implant from its pre-formed cavity, once the implant has been tapped in.

As already mentioned, one of the first embodiment versions has two ribs 30, 32 at radially opposed locations, even though the number of the ribs is arbitrary depending upon the particular application of the implant 20. In most cases, however the spacing of the ribs about the axis 38 is uniform, i.e. in case of two ribs, 180°, in case of four ribs, 90° etc.

The size of the core 22 and of the ribs 30-32 is compatible with the shape and size of a socket formed in the respective bone, so that the individual parts of the implant 20 contact the walls of the socket when the implant has been tapped in, as will be described later.

In summary, therefore, the anchoring projections or ribs 30-32 may extend only over the axial length of the core 22 or, in a second embodiment, may extend beyond the second end 26. The ribs may have the configuration of a generally solid rib-like projections or may have a series of back biting plate-like fins over at least a portion of their length.

The socket configured to receive the implant described above is produced by utilizing template means which includes a template means 50 an exemplary embodiment of which is depicted in FIGS. 3 to 6. It includes a generally template 50 formed by a cylindric sleeve 52 which has a first end 54, a second end 56, an inner wall 58 and an outer, circumferential wall 60. The outer diameter 62 of the outer or circumferential wall 60 corresponds to the diameter of the core 22 of the implant and also of an associated pre-drilled bore 76 to which a further reference will be made later. Provided in the cylindric outer wall 60 are two axially elongated channels 64, 66, 68, 70, also described, for convenience, as a first, second, third and fourth channel, respectively. The channels are spaced from each other at an angle of about 90° about the axis 53 of the sleeve 52, it being understood that, in certain applications, only two of the channels disposed at diametrally opposite locations, such as channels 64-66 may suffice. It will also be appreciated that a template (not shown) having three channels at a 120° spacing from each other could be provided. The actual number of channels in the outer wall 60 is arbitrary and depends on the application of the present invention which normally determines the diameter 62 of the sleeve 52. The channels 64-70 are concavely rounded as best seen from FIG. 4. The central area of the sleeve 52 defines an opening 58 extending, like the channels 64-70, full length of the sleeve 52, from the first end 54 to the second end 56 thereof. A handle 74 facilitating the handling of the sleeve 52 projects radially from the first end 54 at a location between two adjacent channels 66, 68 so that it does not obstruct the equidistant circumferential spacing between the channels as described. The preferred embodiment of the inventive template means includes, in addition to the template 50, a cylindric locking pin 72 having an outer radius corresponding to that of the concave rounding of the channels 64-70. The length of the pin 72 is greater than the overall length of the implant.

The forming of a socket receiving the first embodiment of the implant will now be described with reference to FIGS. 7-12. The implant 20 only has two rib-like projections 30, 32 and the length of the projections 30, 32 is the same as that of the core 22.

First (FIG. 7), a generally cylindric pre-drilled bore 76 is formed in the bone 78. The bore 76 is compatible in shape with the circumferential wall of the core 22. In the second stage, the template 50 is inserted in the pre-drilled bore 76 as shown in FIG. 8. The circumferential positioning of the channels 64, 66 is set using the lever 74 for adjustments. When the desired location is achieved, a drill is driven into the bone 78 (using the first channel 64 as a guide) to a desired depth. In the case of making the socket for the implant shown only in solid lines of FIG. 1, the depth would only be to the bottom 77 of the bore 76 even though, obviously, as already mentioned, the depth could go beyond the bottom 77 to accommodate the modified version of the implant of FIG. 1 including the parts shown both in the solid and broken lines. This results in the forming of an inwardly open, concavely rounded retaining groove 80 formed in the wall of the bore 76. The shape of the groove 80 viewed in axial direction corresponds to the rounded shape of the rib-like projection 30 of FIG. 1.

In the next step (not shown in the drawings), the drill 79 is withdrawn and, with the template 50 still in, the locking pin 72 is inserted in the circular opening defined partly by the retaining groove 80 and partly by the first channel 64 of the template 50. This locks the template 50 circumferentially of the axis of the bore 76. With the template 50 locked in place, the drill 79 is driven (not shown in the drawings) along the second channel 66 forming a second retaining groove 82. The locking pin 72 and the template 50 are then withdrawn and the shaped socket 84 is ready to receive the implant 20. If desired, the implant 20 may be provided with a growth enhancing coating. The implant 20 is tapped into the socket 84 with the rib-like projections 30, 32 engaging the retaining grooves 80, 82 thus holding the implant 30 in a desired circumferential position, without any excessive radial forces being present.

It will be appreciated that the operation described can be effected in the corresponding fashion using an implant with more than two rib-like projections and correspondingly more retaining grooves formed in the bone or using two or more ribs having free ends projecting beyond the second end 26 of the implant.

Figure 13:
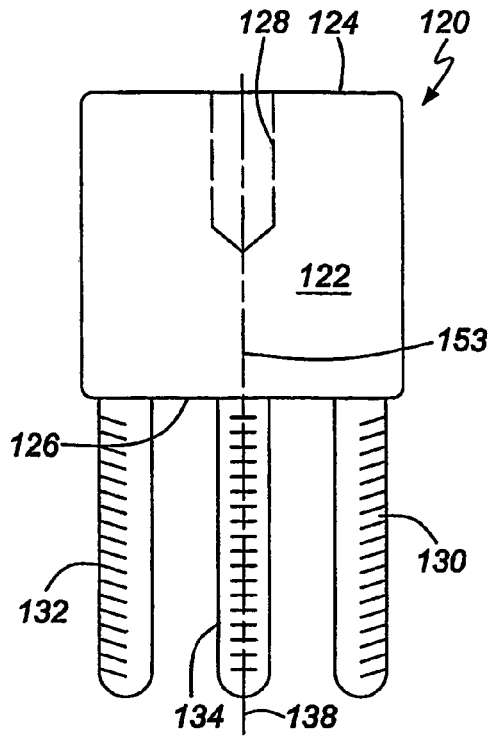
FIG. 13 a diagrammatic side view of another embodiment of the implant of the present invention.
Figure 14:
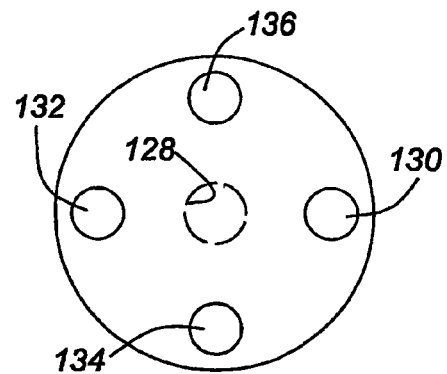
FIG. 14 a bottom plan view thereof.

FIGS. 13, 14 depict a side view of a modified implant 120. Here, instead of the sidewise disposed anchoring projections 30-32, at least two, but possibly four or even more, anchoring stems 130, 132, 134, 136 project downwards from the second end 126 of the core 122 at a radially inward spacing from the diameter of the core 122 of the implant. Otherwise, there is a substantial similarity between the first and second embodiments. As in the first embodiment, the embodiment of the implant 120 comprises a core 122 having a first end 124, a second end 126, a threaded bore 128 and rib-like projections formed in the stems 130, 132, 134 and 136. Similarly, the stems 130-136 are parallel with centreline 138 of the core.

Figure 15:
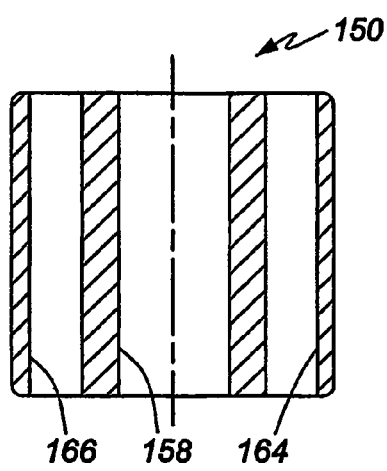
FIG. 15 a sectional view, taken along the section line B-B of a template for forming a socket for the implant shown in FIG. 13.
Figure 16:
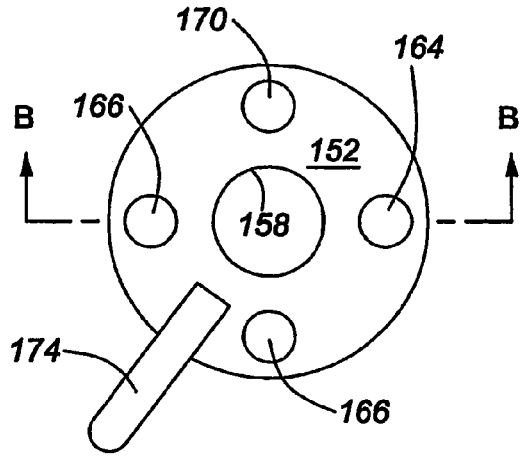
FIG. 16 a top plan view of the representation of FIG. 15.

As shown in FIGS. 15, 16, the template means for forming an implant socket for the implant of FIGS. 13, 14 differs from the first embodiment of the template means by a modified template 150 wherein the drill guiding channels have the shape of cylindric bores or passages 164, 166, 168, 170 through the sleeve 152. The sleeve 152 may be substituted by a solid core of the template 150 even though, the shape of a sleeve 152, having a central opening with an inner wall 158 is preferred as it facilitates the removal of blood and air as the socket is being formed. The template 150 is likewise provided with a handle 174.

The use of the template 150 is analogical to the previously described use of the template 50 and therefore will not be described in detail. Briefly, as in the first embodiment, a bore (not shown) corresponding in size to the generally cylindric core 122 of the implant 150 is pre-drilled, whereupon the template 150 is inserted in the pre-drilled bore and appropriate retaining channels (corresponding, in function, to the retaining grooves 80, 82) are formed for receiving the projections 130, 136. The second embodiment of the template means also includes a locking pin (corresponding to pin 72 and therefore not shown in the drawings). When the first retaining channel, e.g. the one for the projection 130, has been drilled, the locking pin is inserted, much in the fashion of the first embodiment, to circumferentially lock the template 150 in the bore. The remaining retaining channels are then drilled in precisely determined locations of the bottom determined by the location of the channels, such as channels 168, 170 etc.

The embodiments thus far disclosed have a common feature in that the circumferential wall of the core of the implant and the retaining members 30, 32 etc. and 130, 132 etc. are all generally parallel with the centreline of the implant core. In some instances it may be desirable to secure the implant in the bore in a positively locked fashion. This is accomplished by yet another embodiment which will now be described in detail with reference to FIGS. 17-25.

The implant 200 is comprised of two distinct parts: a core 202 and a threaded retainer 204. The core 202 has a first end 206 and an opposite second end 208, both having generally identical shapes of their circumference, so that a circumferential wall 210 extending between the ends 206, 208 is parallel with the centreline 212.

Figure 18:
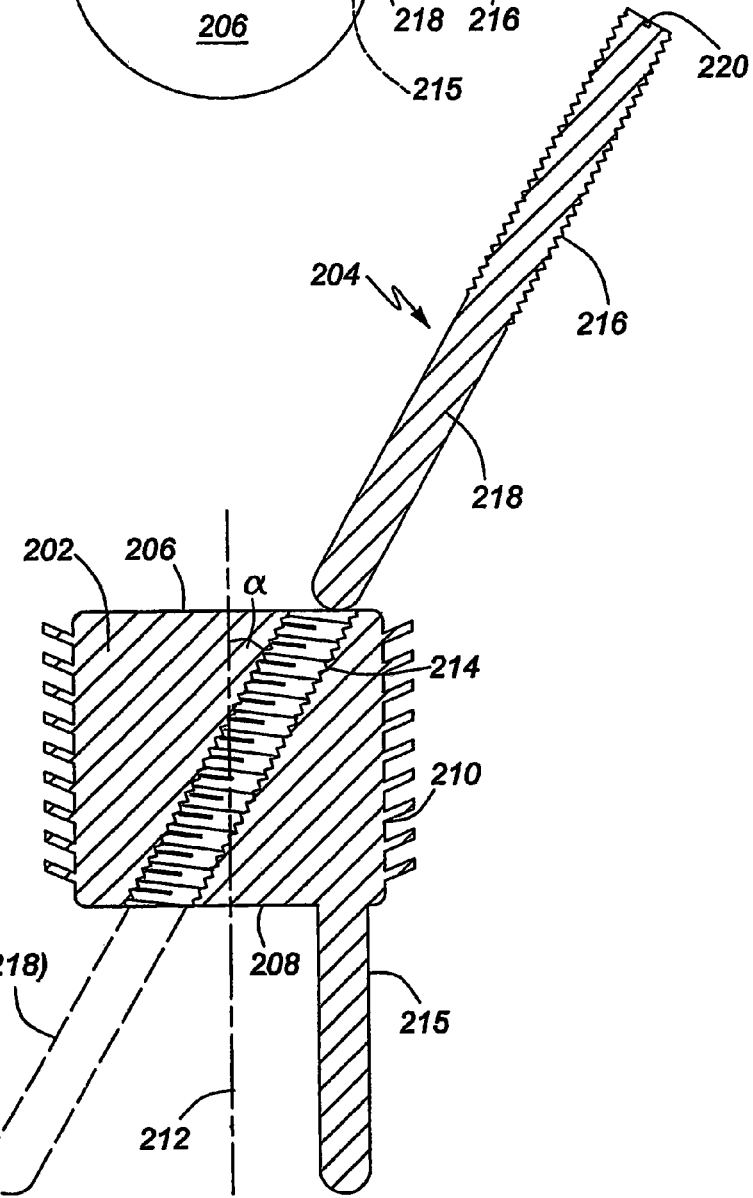
FIG. 18 a simplified sectional view taken along the section line C-C of FIG. 17.
Figure 19:
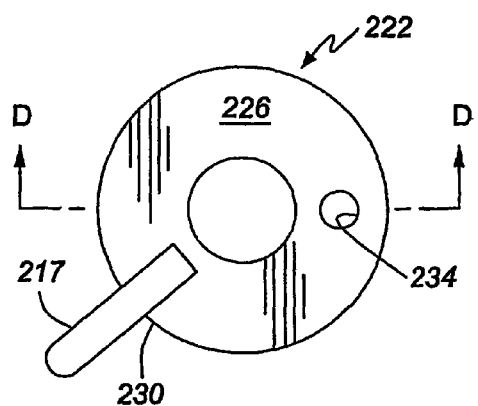
FIG. 19 a top plan view of a first template of template means for forming a bore of a socket for one anchoring stem of the implant of FIGS. 17 and 18.
Figure 21:
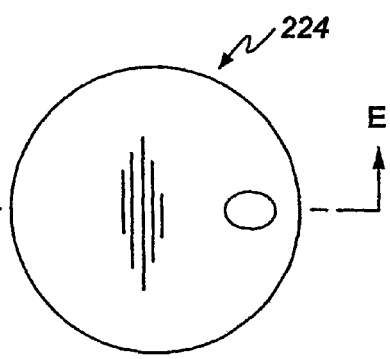
FIG. 21 a top plan view of a second template of template means for forming an oblique bore for an oblique stem of the implant of FIGS. 17 and 18.
Figure 20:
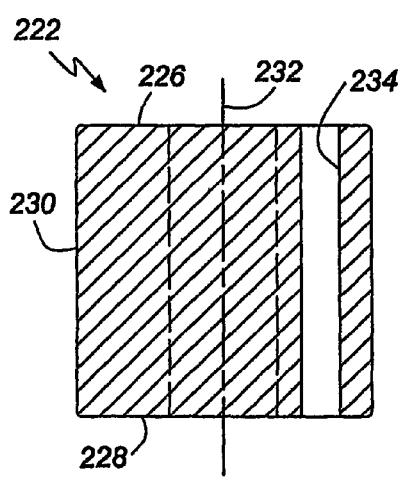
FIG. 20 section D-D of FIG. 19.
Figure 22:
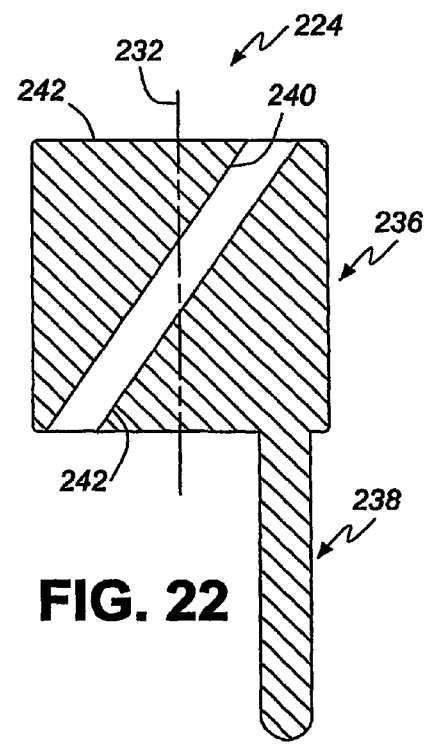
FIG. 22 a sectional view taken along the section line E-E of FIG. 21.
Figure 23:
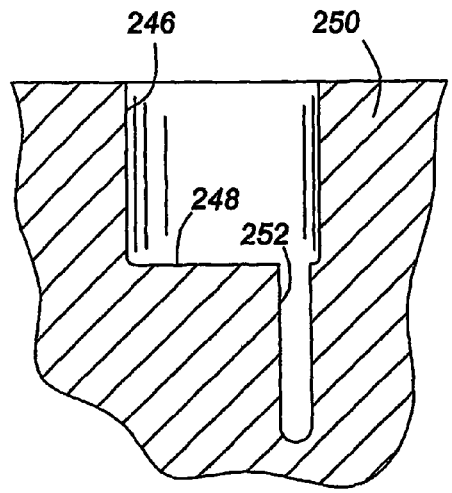
FIG. 23 a sectional view showing the socket finalized by use of the templates of FIGS. 19, 21.

The circumferential wall 210 may be provided, if desired, with back biting fins disposed about the circumference of the wall 210 as diagrammatically shown in FIG. 18. The fins can be each continuous about the circumference of wall 210 or may be in the form of a number of discrete projections uniformly distributed about the circumference and/or axial length of the core 202. For simplicity, the fins are only shown in FIG. 18. It will be understood that the size of the core receiving portion of the socket would be selected to match the maximum diameter of the core.

A threaded bore 214 extends through the core 202 at an acute angle α relative to the centreline 212. The implant 200 is provided with an integrally formed retainer pin 215 projecting from the second end 208 in a direction parallel with the centreline 212.

The threaded retainer 204 has a first portion provided with a thread 216 compatible with the thread formed in the bore 217. The second portion 218 of the retainer 204 has a diameter smaller than that of the threaded portion so that it can freely pass through the threaded bore 214. The free end of the first portion is provided with a suitable screwdriver engaging means, for instance a radial slot 220.

When the implant 200 is fully assembled, the thread 216 engages the thread of the bore 214, while the second portion 218 of the retainer 204 projects from the core 202 at the angle α as shown in broken lines of FIG. 18. In the embodiment shown, the portion 218 projects from the second end 208 of the core 202. It will be understood, however, that in certain applications, depending on the angle α and the axial length of the core 202, the second portion 218 could at least partly extend from the circumferential side wall 210. It will also be appreciated that in certain applications it is possible to provide more than one angled threaded bore such as bore 214. The additional angled bores, of course, would have to be designed such as not to intersect each other.

Thus, in an assembled form, the implant 200 comprises, in addition to the core 200 at least one angled retainer 204 projecting from the core 202 at an acute angle relative to the centreline 212. The inclined position of the retainer 204 secures a positive lock of the implant 200 in a complementary socket.

Figure 17:
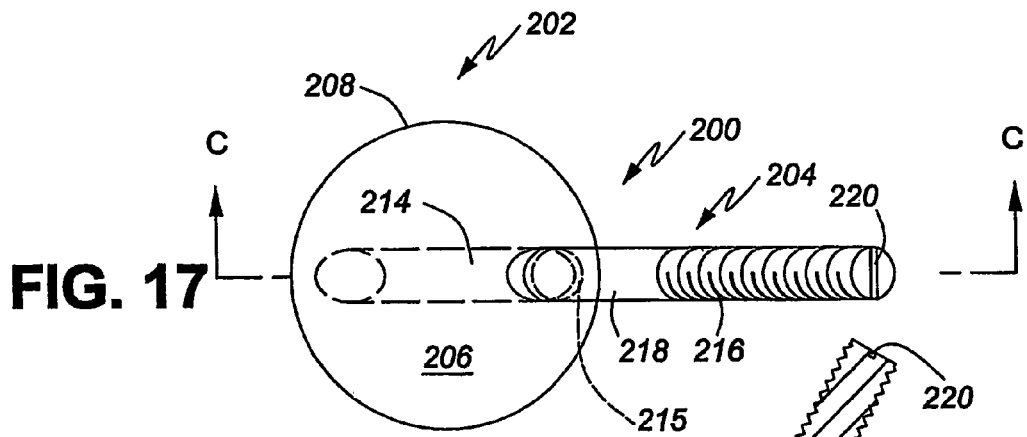
FIG. 17 a top plan view of a bone implant according to a yet another embodiment of the present invention.

The forming of the socket complementary with the implant of FIGS. 17, 18 is effected by means of template means comprising a first template 222 and a second template 224. The first template 222 corresponds in shape and size to the size and shape of the core 202. It has a first end 226, a second end 228 and a circumferential side wall 230 extending between the two ends in a direction parallel with the centreline 232. In the embodiment shown in the drawings, and for the sake of simplicity, the side wall 230 (and thus also the side wall 210) is cylindric. An offset drill guide channel 234 extends between the first and second ends 226, 228 in a direction parallel with the centreline 232 of the first template 222.

The second template 224 has core portion 236 and an integrally formed locking pin 238. An inclined drill guide channel 240 extends between a first end 242 of the core portion 236 and the second end 244 thereof, at the same angle α as referred to above.

Figure 24:
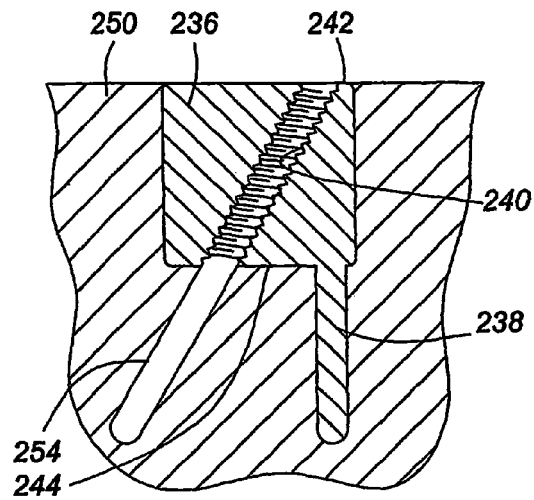
FIG. 24 is a sectional view showing the core of the implant of FIG. 18 tapped in the corresponding socket.
Figure 25:
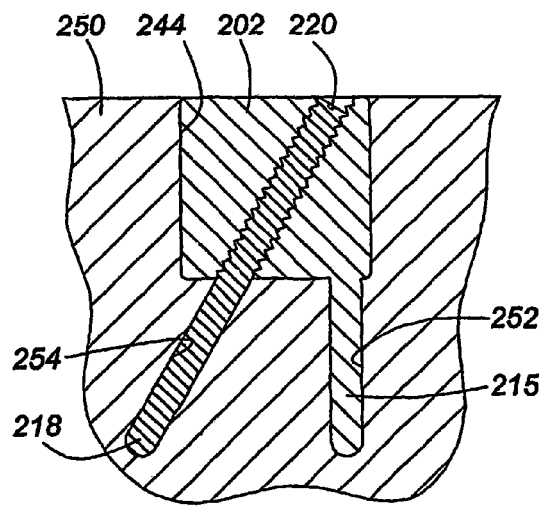
FIG. 25 a sectional view similar to that of FIG. 24 but showing the entire implant with an oblique stem in place.

In operation, a bore 246 having a bottom 248 is first formed in a bone 250. Then, using the first template of FIG. 20, which may be provided with a handle 217 similar to the previously described embodiments, a drill bit (not shown) is guided through and by the channel 234 to form, in the bottom 248, a retainer bore 252 complementary with the lock pin 238 and with the retainer pin 215 of the implant 200. Next, the second template 224 is inserted with its locking pin 238 in the retainer bore 252. A drill is inserted into and guided by the channel 240, and driven into the bone 250, forming the oblique retainer bore 254 compatible with the second end 218 of the retainer 204 (FIG. 24). When the retainer bore 252 is formed, the drill is withdrawn, and the core portion 236 withdrawn from the bore 246, leaving an implant receiving socket shown in FIG. 23. The core 202 with the retainer pin 215 are now inserted into the socket. With the core 202 and retainer pin 215 in place, the threaded bore 214 is automatically aligned with the oblique retaining bore 254, ready to receive the retainer 204. The second portion 218 of the retainer 204 may be provided with a growth enhancing composition and the thread 216 with a suitable sealant, whereupon the retainer 204 is simply threaded into the core 202, whereby the implant 200 is positively locked in the preformed socket, as shown in FIG. 25.

Figure 26:
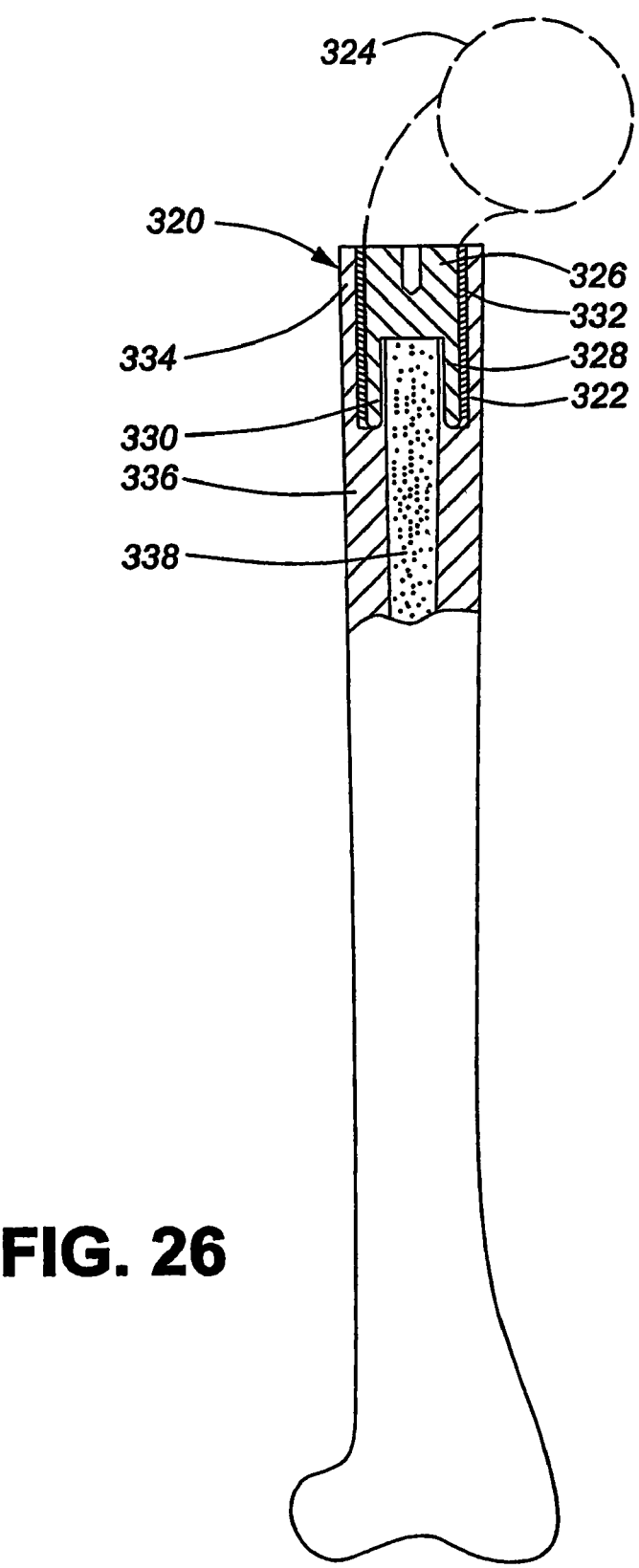
FIG. 26 a sectional view showing the use of the invention in providing an anchor for the head of an artificial hip joint in a femur.

As already mentioned, the exemplary embodiments thus far described are dental implants, it being understood that the inventive method, implant and template means can also be utilized with advantage in a different field, as shown by way of an example, in FIG. 26.

Here an implant 320 is shown in a femur. It has the configuration similar to but correspondingly different in size from, the implant of FIGS. 1 and 2. The implant 320 includes extensions 328, 330 of rib-like projections 332, 334. Additional ribs, not shown but corresponding in location to ribs 34, 36 and their respective extensions can also be provided. The implant shown provides a securement to the femur-322 of an artificial hip joint head 324. The socket for the implant 320 is drilled in the same fashion as described with reference to the template of FIGS. 3 and 4. It will be observed, however, that the rib-like projections and their extensions are embedded in the bone tissue 336, not in the marrow 338 as is the case of most femoral prostheses. This results in a reduced damage to the bone marrow 338 and thus to the red blood cell formation in the femur 322. Also, the tapping of the implant into the bone marrow does not produce excessive radial forces as the socket for the implant is pre-formed before the insertion.

The embodiment described in the preceding paragraph is intended to demonstrate that the present invention can be used in fields other than dental implants.

Figure 8:
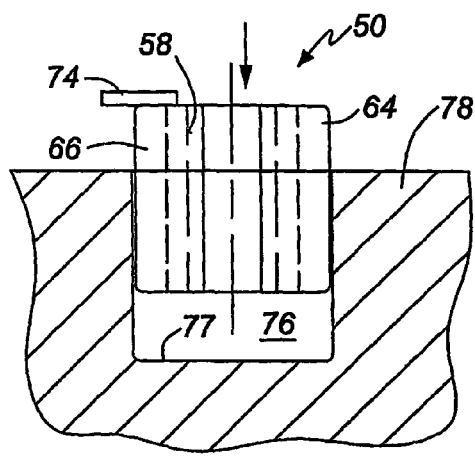
FIG. 8 a section similar to that of FIG. 7 but with the template partly inserted.
Figure 9:
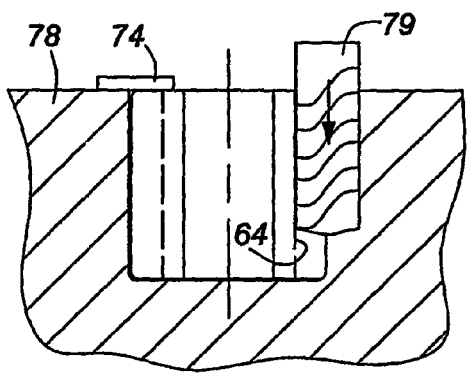
FIG. 9 a section similar to FIG. 8 but showing the template in place and one of retaining grooves being drilled.
Figure 10:
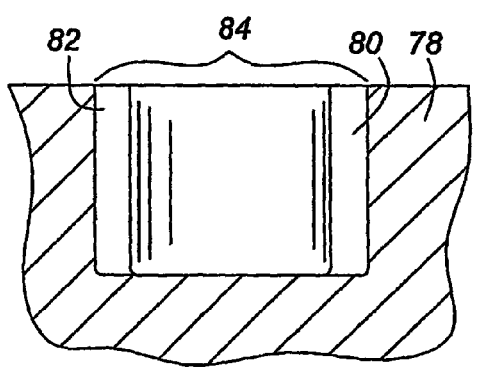
FIG. 10 a section similar to FIG. 9 showing the socket for the first embodiment of FIG. 1 in its final shape.
Figure 11:
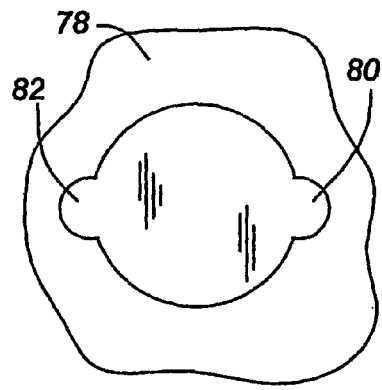
FIG. 11 a top plan view of FIG. 10.
Figure 12:
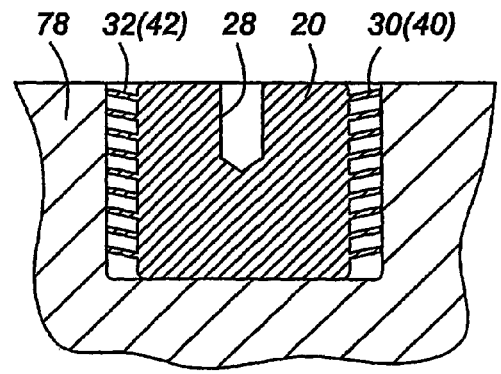
FIG. 12 a section view showing the implant tapped in the socket.

For simplicity, the core 22, 122, 202 and 326 are all shown as having a cylindric configuration which has the advantage of the formation by simple pre-drilling of the bore such as bore 76 in FIG. 7. The circular cross-section of the bore necessitates the locking of the correspondingly cylindric template at an exact circumferential position by the locking pin 72, 238 or by some more complex and not preferred or described securement. While the locking of the cylindric core as described, using the locking pin mechanism, provides the required accuracy, the resistance of an implant to an undesired subsequent circumferential displacement or rotation of the core can be further enhanced by utilizing a core having other than circular cross-section, for instance oval or rectangular with rounded corners.

Figure 27:
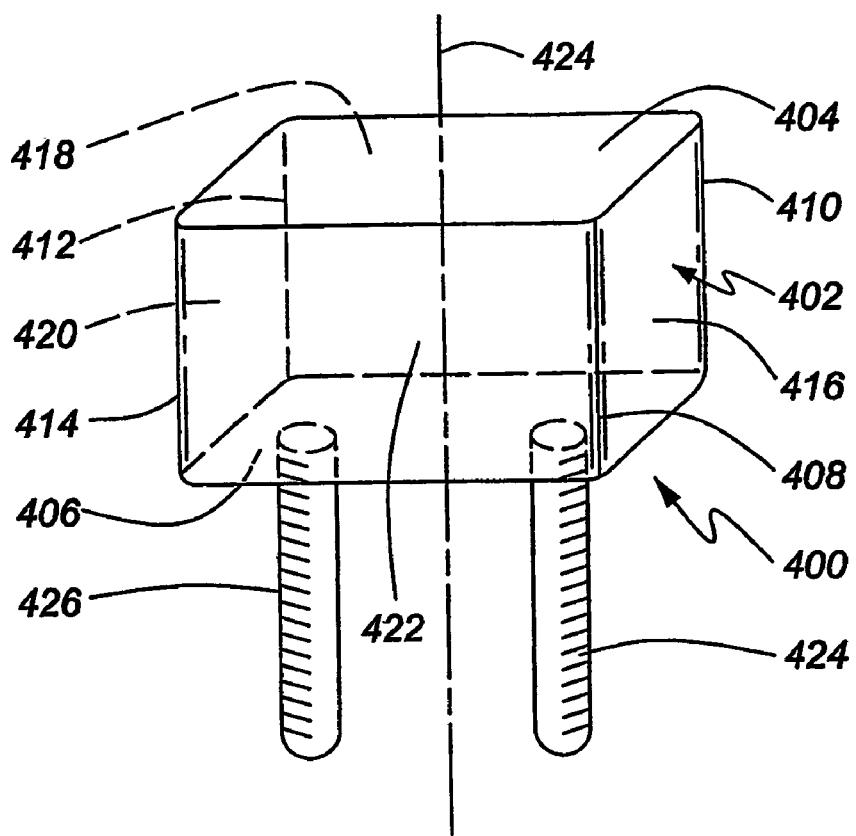
FIG. 27 a perspective view of yet another embodiment of the implant.

FIG. 27 shows a perspective view of still another embodiment of an implant 400 of the present invention, in which the core 402 has a first end 404 and a second end 406. The cross-sectional configuration of the core 402 is rectangular with rounded outer corners 408, 410, 412, 414 between generally rectangular side walls 416, 418, 420, 422 all of which extend between the ends 404-406 in a direction parallel with the centreline 424 of the core 402. Two retainer stems 425, 426 extend from the second end 406.

The template means for forming a socket for the implant of FIG. 27 includes a first template and a second template.

Figure 29A:
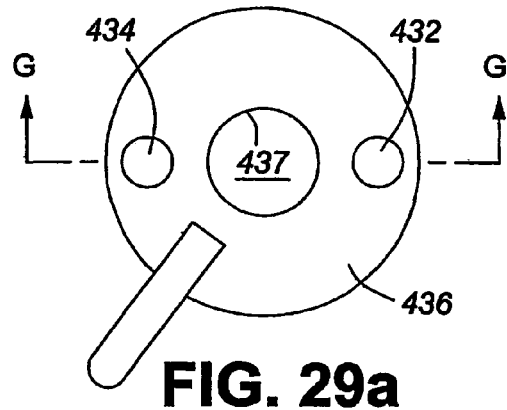
Figure 29B:
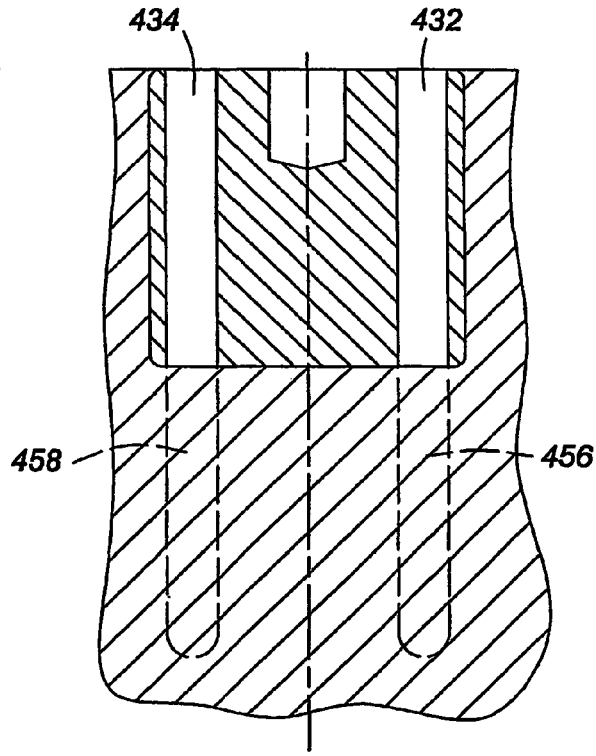
FIG. 29b is a cross-sectional view taken along section line G-G of FIG. 29a and showing the template of FIG. 29a placed in a pilot bore of FIG. 28a, with an indication of retaining bores eventually drilled through drill leading bores of the first template.

The first template (FIGS. 29a, 29b) is similar to the template of FIG. 16. It is provided with two drill guiding channels 432, 434 having the shape of cylindric bores or passages through the sleeve 436. As in the previous embodiment of FIG. 16, the sleeve 436 may be substituted by a solid cylinder. However, the shape of a sleeve 436 having a central opening defining an inner wall 437 is preferred as it facilitates the removal of blood and air as the socket is being formed.

The second template is somewhat similar to the structure of the implant of FIG. 27. It mainly differs in that the core 438, while also having the shape of a prism, is of a smaller size when viewed in the direction of the centreline 440 (FIG. 30b). Projecting from a second end 442 of the core 438 is a pair of anchor stems 444, 446. The core 438 of the second template has a rectangular circumference having four side walls 448, 450, 452 and 454 which adjoin each other at rounded corners.

Figure 28A:
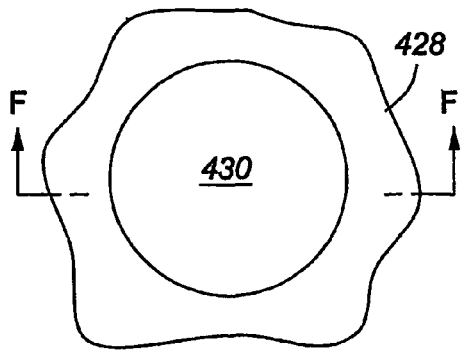
FIG. 28a a top plan view of a pilot bore drilled in a bone, in preparation of forming the socket for the implant of FIG. 27.
Figure 28B:
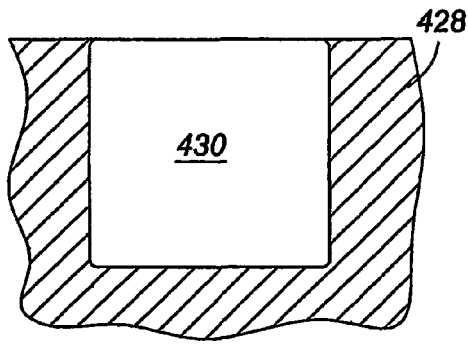

The socket is formed by first drilling in a bone 428 a cylindric pilot bore 430 (FIG. 28a, 28b) of a relatively small diameter which corresponds to the outer diameter of the first template. The first template is then inserted into the bore 430 and, utilizing the guide channels 432, 434, retaining bores 456, 458 are drilled to extend from the bottom of the pilot bore 430 at a spacing from each other corresponding to that of the guide channels 432, 437 which, in turn, corresponds to the spacing between the retainer pins 424, 426 of the implant. A locking pin similar to that previously described can be used after one of the two bores, to prevent undesired turning of the first template while forming the second bore.

Upon withdrawal of the first template from the pre-formed socket, the second template is inserted in the pilot bore 430. This is shown in FIGS. 30a through 31b. It will be noted from FIG. 30a that the diameter of the pilot bore 430 equals the length of the diagonals of the rectangular core 438 of the second template, as viewed in axial direction. The stems 444, 446 are disposed in the retaining bores 456, 458 preventing the second template from turning within the pilot bore 430.

Figure 32A:
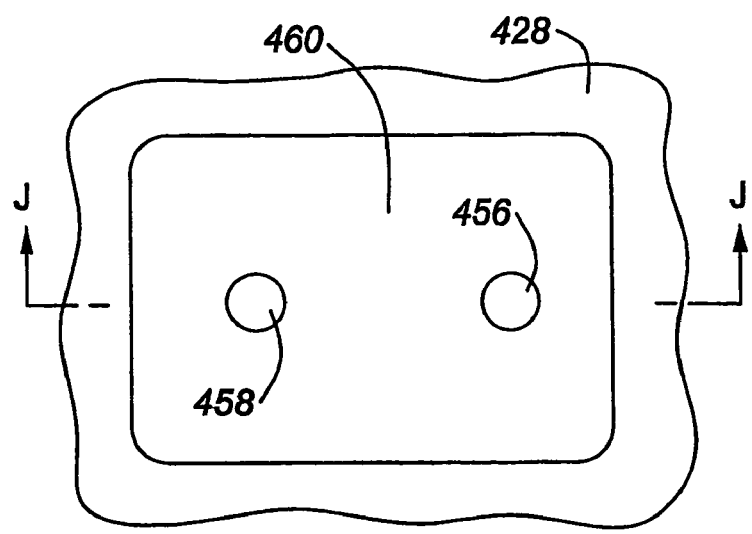
FIG. 32a a top plan view of a finished socket for the implant of FIG. 27.
Figure 32B:
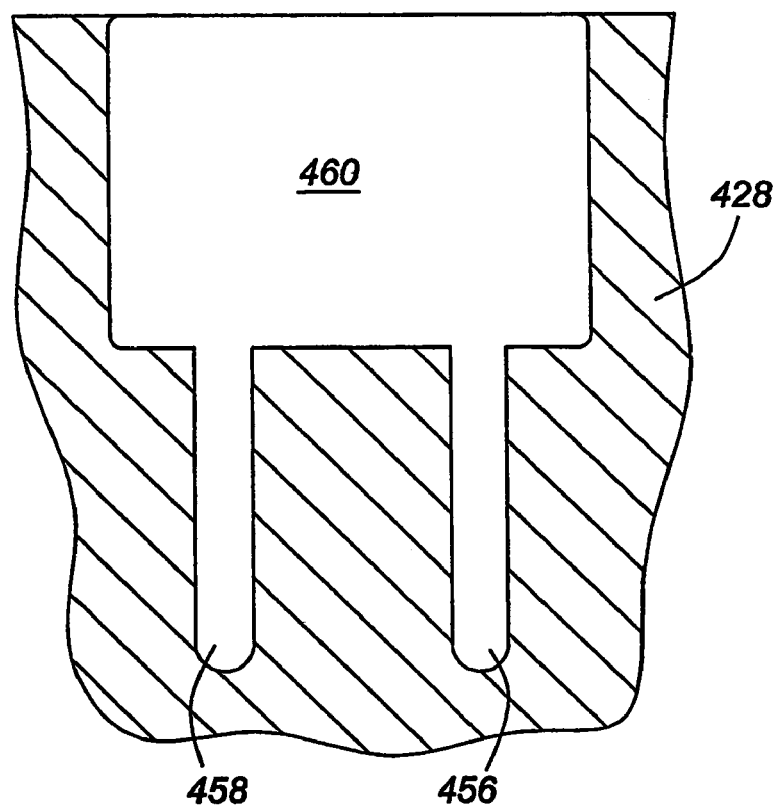

The circumferential surface of the core 438 provides a guide for a router 445 (FIG. 30a) cutting a rectangular bore 460 (FIG. 32a). When the circumferential shape of the rectangular bore 460 is finished, the second template is withdrawn and the socket is ready for tapping in the implant of FIG. 27, the core 402 in the rectangular bore 460 and the retainer stems 424, 426 in the retaining bores 456, 458.

The rectangular cross-sectional configuration of the core 402 compatible with the bore 460 provides additional resistance of the implant to torque stress.

As mentioned at the outset, the drawings of the present application present diagrammatic, simplified representations of different embodiments of the present invention thus far described. Thus, for the sake of simplicity, the bores accommodating the core of the associated implant are indicated as having a flat bottom while, in an actual shape, the bottom of the bores would often be shallowly concavely conical, depending on the tool used in forming same.

In a further development of the present invention, it has been realized that the actual shape of the bores can be advantageously modified by using different tools for the formation of the socket. This development will now be described in detail with reference to FIGS. 33-47, by way of an exemplary embodiment of the tools, an implant and a method of preparing a socket for a dental implant.

The tools for the forming of the socket include at least one drill bit, at least one but preferably two core forming shaped bits and a template.

Turning firstly to FIG. 33, reference number 500 designates a drill bit. As is well known the drill bit comprises a stem 502 provided, at a free end thereof, with a spiral convolute 504 extending all the way to the free end tip 506. The opposite, root end of the stem 502 is provided with an integrally formed latch fitting 508. As is well known, the fitting 508 serves the purpose of latching the bit 510 to a dental drill. Typically, in the art of dental implants the diameter of the bit 500 would be about 1.5 mm. The bit is provided with an abutment ring 509 which may be axially adjustably secured to the stem 502. For instance, a setscrew in a radial threaded bore (not shown in the drawing) can be provided to firmly connect the ring 509 at a selected axial location of the stem 502. Many other alternatives are well known of the abutment means for limiting the maximum depth of the bore produced by the bit 500.

Reference should now be had to FIGS. 36 and 37 wherein the numeral 510 designates a first shaped bit 510. The bit 510 is somewhat similar in shape and function to what is commonly known as a spade bit. The structure of the bit 510 includes a shank 512 and a smooth cylindric free end stem 513 terminating in a rounded free end tip 514. As in the bit of FIG. 33, there is a latch fitting 516. Preferably, the stem 512 and shank 513 are integrally formed. Two cutting plates 518, 520, having the shape of a mirror image of each other, disposed between the shank 512 and stem 513 project from radially opposite sides at a location between the shank 512 and the stem 513. Preferably, the plates 518, 520 are integrally formed with the shank 512 and stem 513. Each plate 518, 520 has a sharpened, concavely curved cutting edge 522, 524 turned towards the free end tip 514, and a side edge 526, 528, generally parallel with the axis of the shank 512. As already mentioned, the plates 518, 520 are a mirror image of each other. Accordingly the corners between the respective cutting edges and the side edges 522-526, 524-528 are equidistantly spaced from each other. The axial distance from the tip 514 to the cutting edges 522, 524 is predetermined as will be mentioned.

FIGS. 40, 41 show a second shaped bit 530. The overall configuration of the second shaped bit 530 corresponds to that of the first shaped bit 510. However, the cutting plates 532, 534 have a different shape and disposition. Each cutting plate has a generally identically, concavely shaped first cutting edge 536, 538. However the edges are spaced from the rounded tip 540, a distance which is smaller than in the embodiment of FIG. 36. The opposed side edges 542, 544 of the plates 532, 534 are spaced radially from each other the same distance as the side edges 526, 528 of FIG. 36. However, in axial direction, they are longer than the edges 526, 528. Furthermore, the ends of the side edges 542, 544 terminate each in a short oblique by outwardly directed straight, cutting edge 546, 548. The shank 550, the plates 532, 538 and the stem 551 otherwise correspond to the structure of the corresponding parts of the shaped bit of FIG. 36.

Both the stem 513 and 551 have the same diameter corresponding to that of the drill bit 500.

FIGS. 46 and 47 show a template 552 for finishing the socket pre-formed by the above tools. In particular, the template 552 serves the purpose of guiding a drill bit (not shown) to provide bores for projections of the implant which will be referred to hereinafter. The template 552 is very similar, but not identical, to that of FIGS. 15, 16. It has the drill guiding channels having the shape of cylindric bores or passages 554, 556, 558, 560 through the sleeve 562, and a central opening 564. And there is a handle 566 as in the previously described embodiment. The only difference is in the shape of the second end of the sleeve remote from the handle 566. The second end is concavely shaped at 568 at a radius corresponding to the radius of the cutting edges 536, 538 (FIG. 40).

FIGS. 34 and 35 show the forming of a small diameter pilot bore 570 in a bone 572. In FIG. 34, a stage is shown where the bore 570 has been bored by the drill 500 to a predetermined depth determined by the axial distance of the ring 509 from the tip 506 of the drill. In FIG. 34, the drill bit 500 is being withdrawn from a pilot bore 570. FIG. 35 shows the finished pilot bore 570 ready for further forming of the implant socket.

FIG. 38 shows the use of the first shaped bit 510. Using the previously formed (FIG. 35) pilot bore 570 as a guide for the stem 513, the cutting edges 522, 524 of the plates 518, 520 form an upper portion of an enlarged bore 574 (FIG. 39). As in most of the preceding embodiments, the diameter of the bore 574 is compatible with the diameter of an associated template, in this case template 552. It is noteworthy that the bottom 576 (FIG. 39) is convexly shaped thus saving a volume of bone tissue which, in the previously described embodiments, is cut off and thus wasted. Furthermore, it is shown in FIG. 38 that the depth of the upper portion of the bore 574 is determined by the depth of the pilot bore 570. When the tip 514 reaches the bottom of the pilot bore, the desired depth of the upper portion of the bore 574 has been reached.

In the next step, the rotating second shaped bit 530 is inserted in the preformed upper part of the bore 574 and the drilling of the bore 574 continued. Eventually, the free end 540 of the stem 551 (which is shorter than its counterpart of bit 510) reaches the bottom (FIG. 42) of the short remainder of the pilot bore 570 whereby the desired depth of the enlarged bore 574 is reached. Preferably, the concave curvature of the cutting edges 536, 538 of the second shaped bit 530 is the same as that of edges 522, 524 of the first shaped bit. It is apparent from FIG. 42 that when the tip 540 reaches the bottom of the pilot bore 570, the oblique cutting edges 546, 548 will have cut a small bevel 578 at the opening of the bore 574 which facilitates the insertion of an associated template such as template 552 and, eventually, of an associated implant such as implant 580 shown in FIG. 44.

The exemplary implant 5 of FIGS. 44, 45 corresponds in overall configuration to that of FIG. 13. At least two, in the embodiment shown, four projections 582, 584, 586, 587 project axially away from the lower end 590 of the core 592 at a radially inward spacing from the diameter of the core 592. The important difference is in that the lower end 590, instead of being generally flat, is concavely shaped in conformity with the shape of the bottom 576 of the finished enlarged bore 574. As diagrammatically indicated in FIG. 44, if desired, the projections 582-588 may be provided with oblique, back biting fins previously described. This also applies to any of the corresponding projections of the implants previously described.

The bores of the socket for receiving the projections 582-588 are drilled using the guide channels 554-560 of the template of FIG. 46, 47 and, possibly, also using a locking pin such as the pin 72 when the first of the four bores has been formed. Once the projection bores are drilled, the formation of the socket is finished and the socket is ready for the implant to be tapped in.

The advantage of the last described embodiment is seen in that, firstly, it avoids unnecessary removal of bone tissue. Also, the plate-like shape of the cutting plates allows for a much better access for the cooling water or other coolant while drilling the opening for the core of the implant. This further reduces damage to the bone tissue by burning which may occur in case of a relatively limited access of the coolant through the spiral grooves of the regular drill bit.

Those skilled in the art will readily appreciate that in the last described embodiment of the forming of the socket, the template of FIGS. 46 and 47 is to be considered as an exemplary embodiment since other described templates with the correspondingly modified core of the implant can be used, all utilizing the reduced loss of bone tissue. Also, only one shaped bit 530 can be used eliminating the use of the bit 510, even though the use of two separate bits is preferred.

The numerous embodiments of the implants and templates disclosed are to be considered as presently preferred embodiments of the invention which, however, can be modified to differ from what has been described, without departing from the scope of the present invention as set forth in the accompanying claims.

What is claimed is:

1. A bone implant comprising:
   (a) a core having a first end wall, a second end wall and defining a centerline extending centrally of and between said end walls, and a circumferential side wall portion parallel and extending between said end walls;
   (b) at least two axially elongated projections,
      (i) extending from the second end wall
      (ii) being disposed at a uniform circumferential spacing from each other about the centerline,
      (iii) having a rounded contour when viewed in axial direction of the core, and
   wherein each projection is formed with a plurality of fins along said core and projecting radially outwards beyond the circumferential side wall portion of said core and which are disposed in a row parallel with said centerline; and
   (c) said core and said projections being dimensioned to contact inner wall sections of a socket formed in a bone, said socket having a predetermined size and configuration compatible with that of the implant, when the implant has been tapped into the socket.

2. The bone implant of claim 1, comprising four axially elongated projections, said projections being disposed at a generally 90° circumferential spacing from each other about said centerline.

3. The bone implant of claim 1, further comprising at least two elongated stems extending from a location at the second end wall of said core and having a free end disposed beyond said second end wall, each stem defining a stem axis.

4. The bone implant of claim 3, wherein a part of each elongated stem has a radially outer portion which forms an extension of one of said projections.

5. The bone implant of claim 3, wherein at least a part of at least one of the elongated stems includes a plurality of fins inclined in a direction toward the axis and the free end of the respective stem whereby the tapping of the implant into the socket is facilitated and the withdrawal thereof from the socket is impeded by back biting orientation of the fins.

6. The bone implant of claim 1, wherein the fins are inclined in a direction toward the centerline and the second end wall, whereby the tapping of the implant into an associated socket is facilitated and the withdrawal thereof from the socket is impeded by back biting orientation of the fins.

7. The bone implant of claim 1, wherein said circumferential side wall is generally circular in a cross-section perpendicular to said centerline.

8. The bone implant of claim 1, wherein said second end wall of the core has the shape of a cavity symmetrical according to said centerline.

9. The bone implant of claim 8, wherein the shape of the cavity is concave.

10. The bone implant of claim 1, wherein the first end of the core is provided with a securement means for fixing a prosthesis or healing cap to the core.

11. The bone implant of claim 10, wherein the securement means comprises a threaded bore for fixing the prosthesis or healing cap to the core.

12. A method for inserting the implant of claim 1 into an implant-receiving socket in bone, which comprises:
   forming the implant receiving socket from a bore pre-formed in a bone, using template means comprising:
   (a) a sleeve having an axis, a first end, a second end, an inner wall and an outer wall, an outer circumference of the sleeve corresponding in shape and in size to the circumference of an associated bore pre-formed in the bone;
   (b) an axially elongated first channel and an axially elongated second channel, each formed in the outer wall of the sleeve, having a concavely rounded cross-section and being disposed at a generally uniform spacing from each other about said axis; and
   inserting the implant into the implant receiving cavity.

13. The method template means of claim 12, wherein the template means further comprises a generally cylindrical locking pin discrete from the sleeve and compatible with the radius of one of said grooves.

14. The method template means of claim 12, wherein the template means further comprises a third channel and a fourth channel, all said channels being formed in the outer wall of the sleeve at a spacing from one another of about 90° about said axis, each channel having a generally semi-circular cross-section.

15. The method template means of claim 12, wherein the template means further comprises a handle disposed at said first end of the sleeve between two adjacent channels and projecting radially away from the sleeve to facilitate manipulation of the sleeve.

16. The method template means of claim 12, wherein the channels of the template means extend full length of the sleeve, from the first end to the second end thereof.

17. The method template means of claim 12, wherein the locking pin of the template means is a tubular sleeve.

18. The method template means of claim 12, wherein the second end of the sleeve of the template means is concavely rounded.

* * * * *